US006855535B2

(12) United States Patent
Meyer et al.

(10) Patent No.: US 6,855,535 B2
(45) Date of Patent: Feb. 15, 2005

(54) METHOD OF LARGE SCALE PRODUCTION OF HEPATITIS A VIRUS

(75) Inventors: Heidi Meyer, Vienna (AT); Manfred Reiter, Vienna (AT); Wolfgang Mundt, Vienna (AT); Noel Barrett, Klosterneuburg/Weidling (AT); Friedrich Dorner, Vienna (AT)

(73) Assignee: Baxter Healthcare S.A., Zurich (CH)

( * ) Notice: Subject to any disclaimer, the term of this patent is extended or adjusted under 35 U.S.C. 154(b) by 0 days.

(21) Appl. No.: 10/006,882

(22) Filed: Dec. 10, 2001

(65) Prior Publication Data

US 2003/0108861 A1 Jun. 12, 2003

(51) Int. Cl.$^7$ .......................... C12N 7/00; C12N 5/00; A61K 39/29

(52) U.S. Cl. ....................... 435/235.1; 435/5; 435/325; 435/364; 424/226.1

(58) Field of Search ......................... 435/5, 235.1, 325, 435/364; 424/226.1

(56) References Cited

U.S. PATENT DOCUMENTS

| | | | | |
|---|---|---|---|---|
| 4,783,407 A | | 11/1988 | Provost et al. | |
| 4,894,228 A | * | 1/1990 | Purcell et al. | 424/89 |
| 5,607,851 A | * | 3/1997 | Pellegrini et al. | 435/236 |
| 5,980,901 A | * | 11/1999 | Shih et al. | 424/189.1 |

FOREIGN PATENT DOCUMENTS

| | | |
|---|---|---|
| WO | WO95/24468 A1 | 9/1995 |
| WO | WO96/15231 A2 | 5/1996 |

OTHER PUBLICATIONS

André, et al. "Inactivated Candidate Vaccines for Hepatitis A" *Prog. Med. Virol.* (1990) vol. 37, pp. 72–95.

Armstrong, et al. "Development of the Formalin–inactivated Hepatitis A Vaccine VAQTA™ From the Live Attenuated Virus Strain CR326F" *J. of Hepatology* (1993) vol. 18, pp. 20–26.

Aunins, et al. "Reactor Development for the Hepatitis A Vaccine VAQTA™" *Animal Cell Technology* (1997) pp. 175–183.

Binn, et al. "Primary Isolation and Serial Passage of Hepatitis A Virus Strains in Primate Cell Cultures" *J. of Clinical Microbiology* (Jul. 1984) vol. 20(1), pp. 28–33.

Bishop, et al. "Rapid and Efficient Purification of Hepatitis A Virus From Cell Culture" *J. of Virological Methods* (1994) vol. 47, pp. 203–216.

Bishop, et al. "Hepatitis A Virus Subviral Particles: Purification, Accumulation, and Relative Infectivity of Virions, Provirions, and Procapsids" *Arch Virol.* (1997)—vol. 142, pp. 2147–2160.

Butler, M. A. Comparative Review of Microcarriers Available for the Growth of Anchorage–dependent Animal Cells *Animal Cell Biotechnology, Ed. R.E. Spier and J.B. Griffiths* (1988) vol. 3, pp. 284–303.

Cohen, et al. "Hepatitis A Virus cDNA and Its RNA Transcripts are Infectious in Cell Culture" *J. of Virology* (Oct. 1987), vol. 61(10), pp. 3035–3039.

Flehmig, et al. "Immunogenicity of a Hepatitis A Virus Vaccine" *J. of Medical Virology* (1987) vol. 22, pp. 7–16.

Junker, et al. "Evaluation of a Microcarrier Process for Large–scale Cultivation of Attenuated Hepatitis A" *Cytotechnology* (1992) vol. 9, pp. 173–187.

Kistner, et al. "Development of a Mammalian Cell (Vero) Derived Candidate Influenza Virus Vaccine" *Vaccine* (1998) vol. 16(9/10), pp. 960–968.

Lemon, et al. "Antigenic Structure of Hepatitis A Virus" *Molecular Aspects of Picornavirus and Detection Ed. B.L. Semler and E. Ehrenfeld* (1989) (1989) pp. 193–208.

Locarnini, et al. "Restricted Replication of Human Hepatitis A Virus in Cell Culture: Intracellular Biochemical Studies" *J. of Virology* (Jan. 1981) vol. 37(1), pp. 216–225.

Nasser, et al. "Production of Cytopathology in FRhK–4 Cells by BS–C–1–Passaged Hepatitis A Virus" *Applied and Environmental Microbiology* (Dec. 1987) vol. 53(12), pp. 2967–2971.

Simmonds, et al. "Persistently Infected Cultures as a Source of Hepatitis A Virus" *Applied and Environmental Microbiology* (Apr. 1985) vol. 49(4), pp. 749–755.

Widell, et al. "A Microcarrier Cell Culture System for Large Scale Production of Hepatitis A Virus" *J. of Virological Methods* (1984) vol. 8, pp. 63–71.

Yokosawa, et al. "Affinity Chromotography of Trypsin and Related Enzymes" *J. of Biochem.* (1976) vol. 79, pp. 757–763.

* cited by examiner

*Primary Examiner*—James Housel
*Assistant Examiner*—Stacy B. Chen
(74) *Attorney, Agent, or Firm*—Townsend and Townsend and Crew LLP

(57) ABSTRACT

The present invention provides methods of large scale production of Hepatitis A Virus (HAV) on VERO cells bound to microcarrier. The invention also provides for methods of isolation of HAV from the cell culture supernatant of HAV infected VERO cells.

13 Claims, 2 Drawing Sheets

Figure 1A:
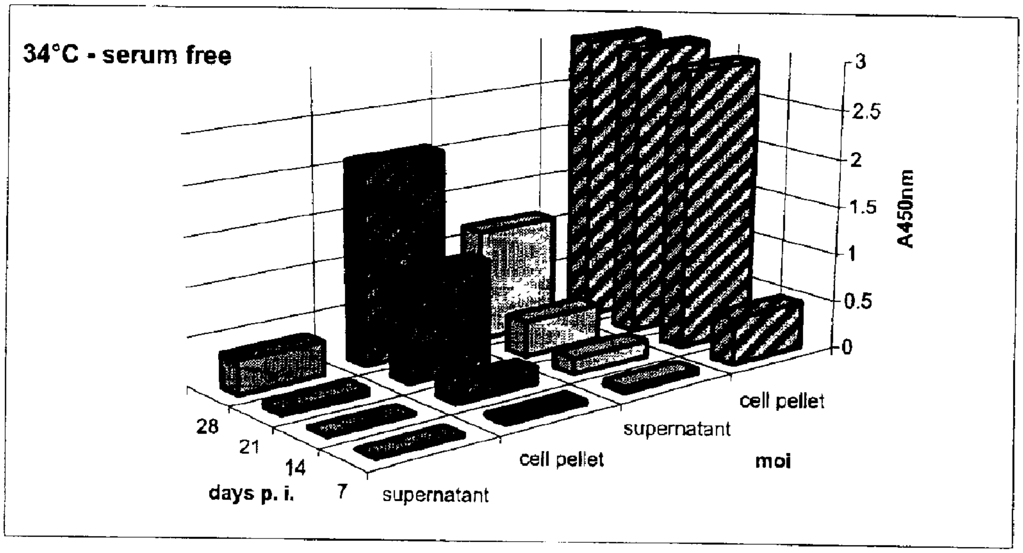
Figure 1A:
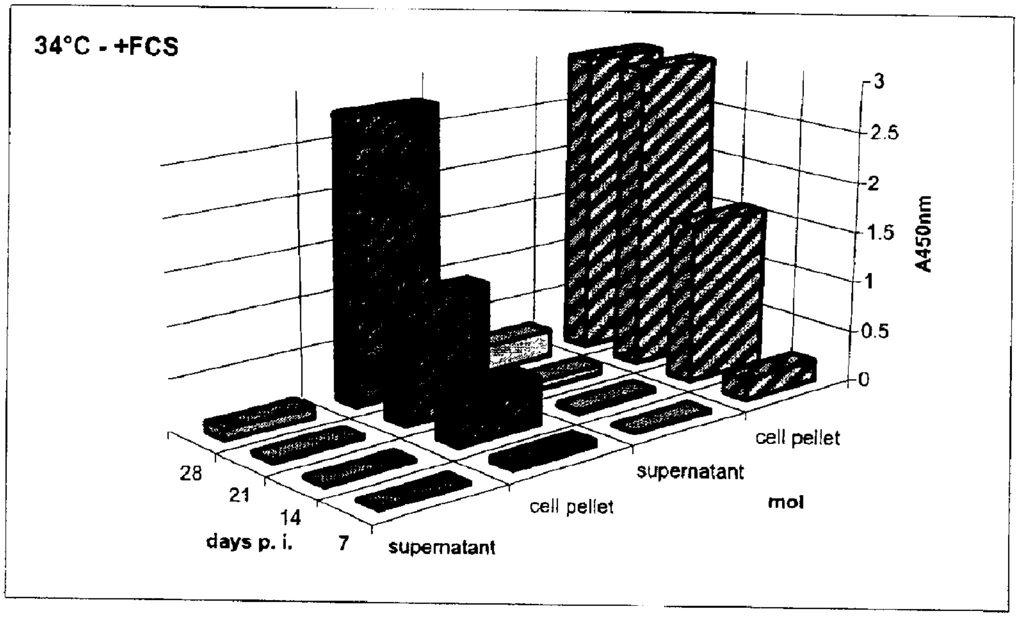

Comparison of different cultivation parameters for the propagation of HAV strain HM175/7 in Vero cells

Comparison of different cultivation parameters for the propagation of HAV strain HM175/7 in Vero cells

METHOD OF LARGE SCALE PRODUCTION OF HEPATITIS A VIRUS

FIELD OF THE INVENTION

The present invention is directed to methods of large scale production of Hepatitis A Virus (HAV) on VERO cells bound to microcarrier. The invention also provides for methods of isolation of HAV from the cell culture supernatant of HAV infected VERO cells.

BACKGROUND OF THE INVENTION

Hepatitis A continues to cause sporadic cases of infection, endemics, occasional deaths and is a public health problem all over the world. The infection is caused by Hepatitis A Virus (HAV) a member of the picornavirus family, a group of small non-enveloped RNA viruses. The virus particle is 27–32 nm in diameter and is composed of three polypeptides cleaved from a single polypeptide precursor molecule. The mature virus is composed of polypeptides VP1, VP2 and VP3. The capsid proteins VP1 and VP3 contain the major antigenic sites and are capable to induce neutralizing antibodies (Lemon et al., 1989, In: Semler et al. eds. Molecular aspects of picornavirus and detection. Washington, D.C.: ASM p 193–208).

Hepatitis A Virus (HAV) is the only hepatotropic virus which can be isolated from cell culture, but the virus is usually difficult to propagate, with long incubation periods and no cytopathic effect. Binn et al. (1984. J. Clincal. Microbiol. 20: 28–33) tested several primate cell types for replication of HAV and optimal conditions for isolation and production of large quantities of virus. Serum free production of HAV was shown in BSC-1 cells, a heterodiploid cell line that until now has not been used for preparation of vaccines for use in humans. After 21 days of culture in roller flasks, virus antigen could be found in the supernatant and the cell fraction. Cells maintained in serum free medium supported viral growth equal to that of cells maintained in serum. A candidate HAV vaccine was obtained from cells and supernatant fluid of infected BSC-1 cells maintained in serum free medium (Binn et al., 1986. J. Infect. Diseases 153: 749–756). However, Simmonds et al. (1985, Appl. Enviromental Microbiol. 49:749–755) found no significant difference of HAV production at different concentration of serum between 2% and 15% in the medium with persistently infected cells BSC-1 or AGMK cells. Virus production in primary AGKM cells was twice that in BSC-1 cells, but HAV produced remained predominantly cell associated and only some virus was found in the culture fluid. Nasser et al. (1987, Appl. Enviromental Microbiol. 53:2967–2971) reported that about seven times more HAV was produced in FRhK-4 cells culture in one-half or less the time that was required for BS-C1 cultures, wherein the ratio of cell-associated HAV versus HAV released BSC-1 cells was calculated to be 80% to 20%, respectively.

Flehmig et al. (1987. J. Medical Virol. 22:7–16) prepared HAV from cell culture supernatant of persistently infected normal human embryonic fibroblasts grown in serum containing medium. Using these methods, large amounts of supernatants were produced in NUNC cell factories and HAV antigen isolated from the supernatant and purified in multiple steps was used for vaccination tests.

Even though several primate cell types have been reported to support replication of HAV, such as fetal rhesus monkey kidney cell line (FRhk-4), primary African green monkey kidney cells (AGKM), continuous African green monkey kidney cells (BCS-1), these cells are generally not used for human vaccine because it is known that monkey kidneys often have high content of latent simian viruses. Other cell lines cannot be used because of the tumorigenic nature of these cells. Mass production of primary human epithelial, fibroblast or kidney cells or cell strains to propagate HAV is also limited by the low passage number of these cells in culture. In fact, the applicable guidelines of the World Health organization (WHO) indicate that only a few cell lines are allowed for virus vaccine production.

One of the cell lines which is currently accepted and validated for the production of vaccine applicable to humans is VERO cells. VERO cells are a continuous monkey kidney cell line that has been licensed for use in the manufacture of human vaccines and is currently used for the production of poliomyelitis and rabies vaccine. Attempts have also been made to use VERO cells for HAV production, but it has been found that replication of HAV on VERO cells is limited because VERO has a temperature restriction of viral growth. In addition, virus is never found in the supernatant fluids of infected cells. (Locarnini et al., 1981, J. Virol. 37: 216–225). U.S. Pat. No. 4,783,407 discloses the production of HAV on VERO cells in roller bottles at a temperature no higher than 33° C. to overcome the temperature restriction. HAV antigen was obtained by freeze-thawing of the cultured cells and release of intracellular produced virus. A commercial vaccine based on propagation of HAV on VERO cells has never been described.

So far, formalin inactivated HAV vaccines have been produced for clinical trials (Andre et al., 1990, In: Melnick (ed): Prog. Med. Virol. Basel, Karger 37: 72–95, Armstrong et al, 1993, J. Hepatology 18: 20–26) and two are commercial available, which induce long-lasting immunity and protection from primary infection. The manufacturing process of the currently available inactivated HAV whole virus vaccines uses the human embryonic lung fibroblast cell line MRC-5 as host cells in Nunc Cell Factories (NCF), wherein the HAV antigen used for vaccine production is obtained form the cell lysate of intracellularly produced virus, because HAV antigen is not efficiently released into the culture supernatant and methods to concentrate the large volume are costly (Bishop et al., 1994. J. Virol. Meth. 47:203–216). HAV large scale preparations from the cell lysates and the cell culture supernatants contain mixed populations of virions and provirions (Bishop et al., 1997. Arch. Virol. 142:2147–2160) and the commercial available vaccine comprises complete mature virions and empty provirion particles (Andre 1990 supra, Armstrong 1993 supra). Moreover, MRC-5 cells grow slowly in tissue culture and require fetal calf serum.

The problems arising from the use of serum in the cell culture and/or protein additives derived from an animal or human source (e.g., the varying quality and composition of different batches and the risk of contamination with mycoplasma, viruses or BSE-agents) are well known. In general, serum or serum derived substances like albumin, transferrin or insulin may contain unwanted agents that can contaminate the cultures and the biological products derived from them. Furthermore, human serum derived additives have to be tested for all known viruses, like hepatitis or HIV, which can be transmitted by serum. Bovine serum and products derived therefrom, for example trypsin, bear the risk of BSE-contamination. In addition, all serum derived products can be contaminated by unknown agents. Therefore, many attempts are being made to provide efficient host systems and cultivation conditions that do not require serum or other serum derived compounds.

The production process is as important as the medium. The only process which is economically feasible is a reactor process because the scale-up can be made appropriate to the market size and the vaccine doses needed. For adherent cells the carrier process with a classical microcarrier is currently the best choice for large scale cultivation of the cells needed for virus propagation. Current processes based on microcarrier culture allow production of viral antigen using fermenter sizes of up to several thousand liters.

Widell et al.(1984, J. Virol. Methods 8:63–71) used microcarrier cell culture systems of FRhk-4 cells for large scale production of HAV and found intra-and extracellular virus. Virus production per cell using the microcarrier system was similar to a conventional culture grown in flask. On the other side, Junker et al (1992, Cytotechnol. 9:173–187) showed that HAV infected MRC-5 cells bound to conventional Cytodex microcarriers only yielded 30% HAV antigen compared to cells grown in flasks because of the tendency of MRC-5 cells to form microcarrier and cell aggregates. WO 95/24468 discloses MRC5 cells grown on aggregated glass-coated microcarriers for HAV production in a perfusion system, wherein the bulk of virus is found in the cells. In the system described, higher concentrations of serum between 2–10% allowed greater production of HAV than at low level concentration of 0.5–2% of serum. However, when Aunins et al. (1997, In: Carrondo et al. (eds), Animal Cell Technology, p.175–183) compared different manufacturing technologies such as Nunc Cell Factories (NCF), microcarriers, static mixed reactors and CellCubes, they found that glass-coated microcarriers as described in WO 95/24468 allowed the formation of stable aggregates and production of HAV. The monodisperse microcarrier suspensions, however, could not be maintained for the duration of the culture, and productivity of the glass aggregate microcarrier process was approximately half of static culture under similar conditions. Aunins et al. 1997 (supra) concluded that a microcarrier culture of the HAV strain used was not feasible.

The worldwide market demand for HAV vaccines is in the order of 100 Million doses per year. Efficient vaccine production requires the growth of large-scale quantities of virus produced in high yields from a host system. The process and cultivation conditions under which a virus strain is grown is of great significance with respect to achieving an acceptable high yield of the strain. Thus, in order to maximize the yield of the desired virus, both the system and the cultivation conditions must be adapted specifically to provide an environment that is advantageous for the production of the desired virus. Therefore, a continuing need exists for safe and effective methods to produce viruses and antigen. Moreover, there is a need for an approach to viral propagation, employing materials that are already available and requiring a minimal number of time-consuming manipulations, wherein the selection of a combination of host cells, culture medium, growth conditions and production system is essential to achieve an efficient production process.

SUMMARY OF THE INVENTION

It is an object of the present invention to provide a method of production of HAV antigen.

It is another object of the present invention to provide for a method for production of HAV in serum free or serum and protein free medium.

It is another object of the invention to provide for production of HAV without use of an animal-derived protease during subculture and passaging of the cell culture.

It is another object of the invention to provide for isolation of complete HAV particles.

It is also an object of the invention to provide a serum free or serum and protein free VERO cell culture infected with HAV which continuously produce HAV antigen.

DETAILED DESCRIPTION OF THE PREFERRED EMBODIMENTS

In accordance with these and other objects, the present invention provides a method for continuous production of Hepatitis A virus, comprising the steps of providing a serum free cell culture of VERO cells bound to a microcarrier, infecting said serum free cell culture of VERO cells with HAV, incubating said cell culture infected with HAV to propagate said HAV, whereby HAV is continuously released into the cell culture medium; and harvesting said HAV released into the cell culture medium.

According to the method of the invention, VERO cells bound to a microcarrier are grown under serum free media conditions at a temperature of about 37° C. The cells are grown from the original ampoule of VERO cells to large scale biomass used in a fermenter for large scale production in serum free medium. Prior to infection with HAV the cell culture temperature is reduced to about 34° C. and further virus propagation is performed at this temperature.

The VERO cells can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal cell Biotechnology 3:283–303). For cell culture growth and during virus infection the same microcarrier type can be used. Therefore, according to one embodiment of the invention the serum free VERO cells are cultured and infected on spherical microcarriers. According to another embodiment of the invention the serum free VERO cells are cultured and infected on porous microcarriers. It is also possible to grow the cells to a biomass on a spherical microcarriers and subculture the cells when they have reached final fermenter biomass and prior to infection on a porous microcarrier or vice versa. According to this aspect of the invention the serum free VERO cells are cultured on a spherical microcarrier and infected with virus when the cells are bound to a porous microcarriers. Spherical microcarrier are those selected from the group of smooth surface such as Cytodex I®, Cytodex II® and Cytodex III® (all Pharmacia) and porous microcarriers such as Cytopore®, Cytoline® (all Pharmacia).

The VERO cells bound to microcarrier are infected with HAV at a multiplicity of infection (m.o.i.) between about 0.01 and about 5.

It has been found that under the conditions described above, HAV is continuously released into the cell culture medium supernatant. This was unexpected because prior art using VERO cells as host for HAV disclosed that HAV could only be found intracellularly and virus produced had to be obtained from the cells (U.S. Pat. No. 4,783,407).

The methods of the present invention provide production of HAV, wherein HAV is continuously produced and released into the cell culture supernatant. In the method of the invention HAV can be produced for at least 60 days. The prior art does not describe a cell culture system that continuously produces HAV over such a long period of time. By using a microcarrier culture system and cell culture perfusion, the medium containing the virus is continuously removed from the cell culture and fresh culture medium is added and continuously perfused. The methods of the invention provide large volumes of culture medium comprising HAV which can be harvested and purified from the cell culture supernatant.

The parameters for optimal cell culture conditions are a pH between about 6.5 and about 8.0, a $O_2$ concentration between about 15% and about 40%, a stirring speed between about 20 and about 70 rpm, and a temperature at 34° C. ±0.2° C. or 37° C. ±0.2° C. The culture conditions are preferably kept constant over the complete time period of virus production.

The use of a virus isolate which has been directly obtained from a primary infected cell culture for virus vaccine production bears the risk of contamination by another virus or an unknown agent. The contamination of the virus stock and the cell culture can be avoided by using a virus stock derived from a defined HAV stock.

Any strain of HAV can be produced according to the method of the present invention. According to one embodiment of the invention the cells are infected with an HAV seed virus that is obtained by using a full-length HAV cDNA to in vitro transcribed HAV RNA and infect VERO cells. By using a cDNA encoding for HAV for production of seed virus, a defined, homogenous virus stock is obtained. The HAV used as seed virus and virus stock can be, for example, HAV HM175/7.

Besides serum or other protein additives used for cell cultivation, the addition of trypsin derived from an animal source bears the risk of contaminating the cell culture by unknown agents. Usually, trypsin from an animal source is used during subculture and passaging of cell cultures to obtain cell biomass. To avoid any contaminations derived from an unknown agent or source during HAV virus production process, in the method of the present invention, a protease originated from a microbial source is preferably used for production of cell biomass from the original ampoule.

According to one aspect of the invention the cell culture used for the production of HAV in the present invention is subcultured from the original ampoule to working cell bank and passaged by use of a microbial protease or a trypsin-like activity of a microbial protease.

According to a preferred embodiment a purified trypsin-like enzyme of a microbial protease is used. In particular, the trypsin-like enzyme is *Streptomyces griseus* trypsin (SGT), a purified fraction of Pronase, is used. The purified SGT is preferably obtained by a method of affinity chromatography on benzamidine and elution of purified SGT with an eluting agent comprising about 0.5 to about 1.2 M arginine. It has been found that the SGT purified by this method is very efficient and can be used with reduced protein load to the medium due to its high specific activity. SGT purified from Pronase by other methods known in the art can be used in the method of the invention as well. Such methods include those described by Yokosawa et al. (1976. J. Biochem. 79:757–763) or other chromatography methods.

According to another preferred embodiment of the invention, serum and protein free culture medium is used for cell culture and growth. By using only defined sources, such as minimal medium without addition of serum or proteins as growth additives for cell biomass production and virus propagation, a safe virus vaccine production process is provided.

According to another aspect the invention provides for a method of isolating complete Hepatitis A virus particles, comprising the steps of providing a serum free cell culture of VERO cells bound to a microcarrier, infecting said cell culture with HAV, incubating the cell culture infected with HAV to propagate the HAV, whereby HAV is continuously released into the cell culture medium; harvesting HAV produced and released into the cell culture medium, and isolating complete HAV particles from said HAV harvest of the cell culture supernatant.

The term "complete HAV particle" means RNA-containing HAV particles of mature, infectious HAV virion particles which comprise capsid proteins VP1, VP2 and VP3, and immature provirions which contain VP1, VP3 and VP0 precursor polypeptide.

The complete HAV particles can be isolated by methods well known in the art, such as filtering, centrifugation, sedimentation or chromatographic methods. Centrifugation can be performed on a sucrose-gradient or CsCl-gradient. Prior to centrifugation larger cell fragments can be removed by e.g. filtration.

According to another aspect, the invention provides for an HAV-infected serum free VERO cell culture bound to a microcarrier, wherein the cells bound to the carrier continuously produce and release HAV into the cell culture medium. The HAV-infected cell culture of the invention can release HAV continuously for at least 60 days.

According to a preferred aspect of the invention there is provided an HAV-infected serum and protein free cell culture of VERO cells culture bound to a microcarrier, wherein the cells bound to the carrier continuously produces and releases HAV antigen into the cell culture medium.

Having now generally described this invention, the invention will be understood by reference to the following examples which are provided herein for purposes of illustration only and are not intended to be limiting unless otherwise specified.

EXAMPLE 1

Propagation of HAV on VERO Host Cell System

The HAV strain HM175/7 (kindly provided by Robert Purcell, National Institute of Health, Bethesda, Md.) which has initially been isolated by a clinical specimen and has been serial passaged in primary African green monkey cells, which led to the attenuation of the virus strain, is tested for propagation on VERO cell microcarrier culture.

VERO cells (African Green Monkey, *Cercopthecus aethiops*, kidney) are used as production cell line. The cells have been obtained from the American Type Cell Culture Collection, Rockville, Md. at a passage number 124 under the designation ATCC CCL 81. The cells are adapted to grow in serum-containing, serum-free, or serum- and protein free medium as described in Kistner et al. (1998. Vaccine 16:960–968) or WO 96/15231. For growth in serum free medium a basal DMEM HAM's F12 medium supplemented with inorganic salts, amino acids, sodium bicarbonate (2 g/l) and yeast or soy bean extract (1–10 g/l) is used. The working cell bank is prepared without the use of any animal derived medium components.

One ampoule of a working cells bank (WCB) of VERO cells cultured in DMEM medium mixed with Ham's F12 nutrient mixture in a ratio 1:1 is resuspended in medium containing serum and in serum free medium supplemented either with soy bean or yeast extract (0.1 to 10%). Subculture is performed by using purified Streptomyces griseus trypsin (1 μg/ml) to avoid any agent derived from an animal source which could comprise any pathogenic causing agent. After subculture in Roux and roller bottles 6–8×$10^7$ cells/ gram microcarrier (Cytodex III®, Pharmacia) are inoculated in a 12 l stirred tank fermenter. The cells are grown at 37° C. for 6–8 days. The culture conditions of oxygen saturation 20%+/−10%, pH7.1+/−0.2 are kept constant and stirring speed of 30–60 rpm. On the second day after inoculation at a cell density of $6\times10^5$ to $1\times10^6$ cells/ml a virus suspension of HAV HM175/7 with a multiplicity of infection (m.o.i.) between 0.1 and 1.0 is pumped into the fermenter at a temperature of either 34° C. or 37° C. After two hours to allow for virus adsorption, medium perfusion is started. Half of the fermenter volume is exchanged against fresh medium every day. The microcarrier and the attached cells are retained in the fermenter by a sieve. During the fermentation process pH 7.1, $O_2$ (30%), stirring speed (30–60 rpm) and temperature of 34° C. or 37° C. are controlled.

Figure 1B:
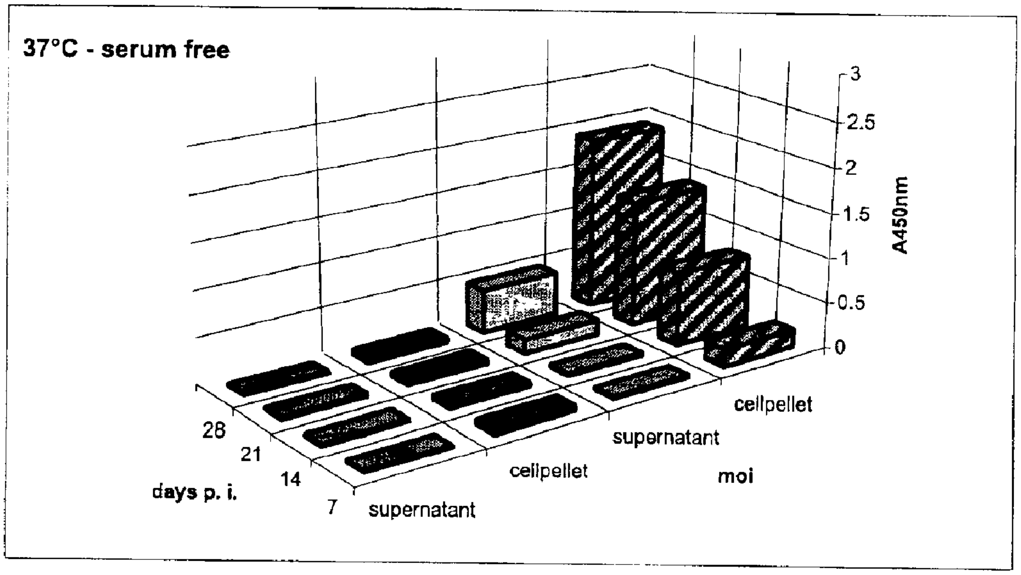
Figure 1B:
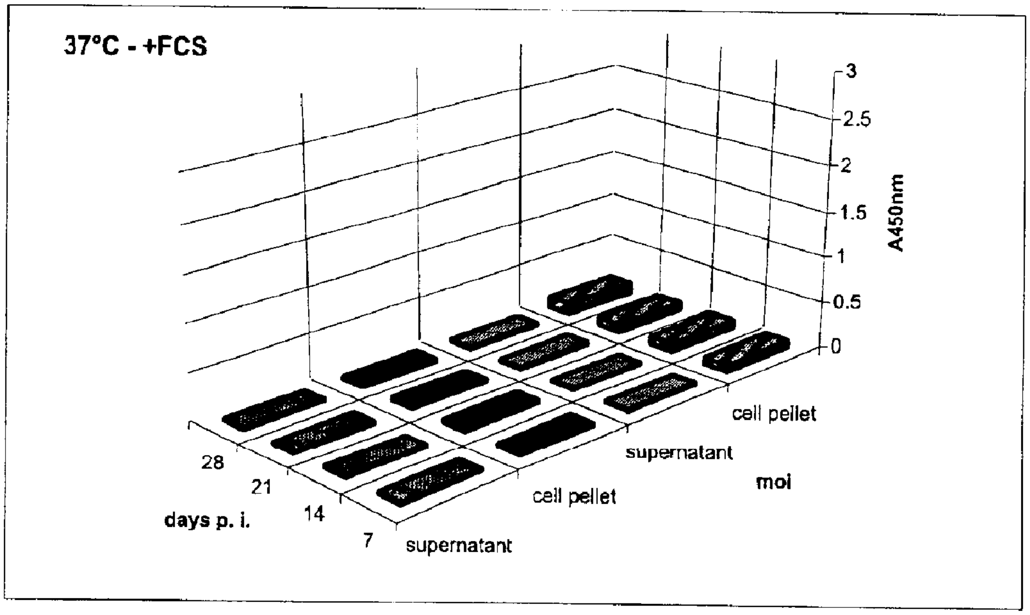

FIG. 1A shows the HAV produced on VERO cells at 34° C. in serum-free medium and serum-containing (FCS) medium. FIG. 1B shows the HAV produced on VERO cells at 37° C. in serum-free medium and serum-containing (FCS) medium. At days 7, 14, 21 and 28 after infection the amount of antigen produced is determined in the cell culture supernatant and in the cell pellet by means of an HAV specific ELISA assay (Mediagnost). The antigen concentration per $10^7$ VERO cells are determined in the cell culture supernatant. The ELISA units (EU) are calculated as the reciprocal value of the highest antigen dilution that gives a positive reaction in the ELISA assay.

HAV strain HM175/7 replicate on VERO cells better at lower temperature of 34° C. than at 37° C., and better in the absence than in presence of serum (FIGS. 1A and 1B). At 37° C. in serum-containing medium no viral antigen production can be observed, wherein at 37° C. in serum-free medium (at higher m.o.i.) virus is produced. Following infection of serum free VERO cells with HAV m.o.i. 0.1 or 1 increased amounts of antigen is detected in the supernatant and cell pellet from the $3^{rd}$ rd week after infection at 34° C. (FIG. 1A). In a cell culture grown at 34° C. in serum containing medium viral antigen is dominantly found in the cell pellet, whereas on VERO cells cultured at 34° C. in serum free medium viral antigen is continuously released in the cell culture supernatant, wherein at about 50% of the viral antigen is found in the supernatant of the culture medium.

EXAMPLE 2

Preparation of HAV Virus Stock for Large Scale Production

Full length cDNA of the genome of attenuated strain HM175/7 cloned in the bacterial plasmid pHAV/7 (Cohen et al., 1987, J. Virol. 61:3035–3039) is used to prepare full length genomic RNA by in vitro transcription. Serum free VERO cells at 34° C. are transfected with in vitro transcribed HAV RNA to generate virus stocks free of adventitious agents. After 6 weeks, HAV specific antigen is detected in the lysate of infected cells which are used to further propagate HAV on VERO cells under serum free conditions. Table 1 shows the antigen and the virus titer produced after serial passages. The infected cells released approximately 50% of the viral antigen in the cell supernatant. After the $4^{th}$ passage, the virus stock has a titer of $8\times10^7$TCID $_{50}$/ml.

TABLE 1

Antigen and Virus Titer of serial passages of HAV strain HM175/7 after transfection of serum free VERO cells

| Passages after | Total Antigen (EU) | | Total Titer ($TCID_{50}$) | |
|---|---|---|---|---|
| transfection | supernatant | cell pellet | supernatant | cell pellet |
| Passage 1 | n.d. | positive | n.d. | n.d. |
| Passage 2 | 16 000 | 25 600 | n.d. | n.d. |
| Passage 3 | 19 200 | 25 600 | $5.2 \times 10^8$ | $4.7 \times 10^8$ |
| Passage 4 | 38 400 | 51 200 | $1.5 \times 10^9$ | $8.9 \times 10^8$ |

The virus stock HM175/7 obtained after serial passages is used for large scale production of HAV antigen on microcarrier system.

EXAMPLE 3

Propagation of HAV HM175/7 on VERO Cells in Serum Free Medium

HAV HM175/7 as obtained according to Example 2 is serially passaged in serum free VERO cells at 34° C. On day 7, 14, and 21 after infection the infectious titer and the amount of antigen is determined (Table 2).

TABLE 2

Propagation of HAV strain HM175/7 on serum free VERO cells at 34° C.

| | Antigen (EU/$5 \times 10^7$ cells) | | Titer ($TCID_{50}$/$5 \times 10^7$ cells) | |
|---|---|---|---|---|
| Passage No. | supernatant | cell pellet | supernatant | cell pellet |
| 7 d | neg. | 1 600 | $1.3 \times 10^7$ | $1.1. \times 10^7$ |
| 14 d | 3 200 | 25 600 | $1.8 \times 10^8$ | $2.3 \times 10^8$ |
| 21 d | 25 600 | 51 200 | $2.1 \times 10^9$ | $5.1 \times 10^8$ |

Virus titers of $5\times10^8$ and $2\times10^9$ per $5\times10^7$ cells are obtained in the cell pellet and the cell culture supernatant, respectively. This demonstrates that viral antigen is persistently released in the cell culture supernatant by the serum free VERO cells. Three weeks post infection (p.i.) the percentage of the viral antigen in the cell culture supernatant is about 50%, while approximately 75% of the infectivity is localized there (Table 2).

EXAMPLE 4

Production of HAV in Serum Free VERO Cells Propagated on Microcarrier

A 6 l fermenter comprising $2\times10^{10}$ VERO cells grown on microcarrier (Cytodex III®, Pharmacia) in serum free medium is infected with HAV strain HM175/7 obtained according to Example 2 with an m.o.i. of 0.5. During a long-term fermentation process at 34° C. the amount of antigen in the cells and in cell culture supernatant is repeatedly determined. For determining HAV produced intracellularly, VERO cells from the cell culture are harvested and adjusted to a cell density of $2\times10^7$ cells/ml in PBS and lysed by three cycles of freeze/thawing. After low speed centrifugation, the infectious titer in the cell debris and the cell culture supernatant is determined as well as the amount of antigen by ELISA assay.

From day 11 after infection onwards increasing amounts of HAV antigen is detected in the cell culture supernatant. The fermentation process is continuously performed and samples are taken over a period of 35 days (Table 3). At this time the cells are still viable and produce HAV antigen. The supernatant from day 23 to 35 is pooled and the total amount of HAV antigen produced is calculated to be $2.5\times10^6$ ELISA units.

TABLE 3

Antigen production of infected VERO microcarrier cell culture

| Days post infection | Cell pellet/ml EU/2 × $10^7$ cell | Supernatant EU/ml |
|---|---|---|
| 1 | 80 | 10 |
| 3 | 80 | — |
| 7 | 160 | — |
| 9 | 320 | |
| 11 | 1280 | 1 |
| 14 | 1280 | 2 |
| 16 | 1280 | 8 |
| 18 | 1280 | 8 |
| 21 | 2560 | 16 |
| 23 | 2560 | 32 |
| 25 | 2560 | 40 |
| 28 | 5120 | 64 |
| 30 | 5120 | 128 |
| 32 | 5120 | 160 |
| 35 | 5120 | 320 |

EXAMPLE 5

Estabishing of Large Scale HAV Production Process

For establishing of large scale fermentation process, different strategies for propagation of HAV are investigated.

Subconfluent VERO cells, propagated under serum free conditions, are seeded on different types of microcarriers of spherical or porous microcarrier, such as Cytodex III®, Cytoline® or Cytopore®, all types being suitable for long-term cultivation process.

Two days after the cells have been seeded on the different types of microcarriers, VERO cells are infected with HAV m.o.i. of 1.0. Cell propagation is performed in a 10 l fermenter at 34° C. with continuous perfusion of growth medium free of serum or free of serum and protein. During the cultivation phase the cell culture supernatant is tested for HAV antigen. The data are summarized in Table 4.

TABLE 4

HAV antigen yield (in EU/ml) after propagation of VERO cells on different microcarriers

| Days after seeding | Microcarrier | | |
|---|---|---|---|
| of infection | Cytodex 3 | Cytopore2 | Cytoline 2 |
| 16 | Neg. | Neg. | Neg. |
| 18 | Neg. | 10 | 4 |
| 21 | 2 | 40 | 2 |
| 23 | 4 | 80 | 8 |
| 25 | 4 | 80 | 16 |
| 28 | 8 | 80 | 8 |
| 30 | 8 | 80 | 10 |
| 32 | 8 | 160 | 20 |
| 35 | 32 | 160 | 20 |
| 37 | 128 | 160 | 40 |
| 39 | 256 | 160 | 40 |
| 42 | 160 | 160 | 40 |
| 44 | 160 | 160 | 40 |
| 46 | 320 | 160 | 40 |
| 49 | 320 | 160 | 80 |
| 51 | 640 | 160 | 80 |
| 53 | 640 | 160 | 80 |

TABLE 4-continued

HAV antigen yield (in EU/ml) after propagation of VERO cells on different microcarriers

| Days after seeding | Microcarrier | | |
|---|---|---|---|
| of infection | Cytodex 3 | Cytopore2 | Cytoline 2 |
| 56 | 640 | 160 | 160 |
| 58 | 1280 | 160 | 80 |
| 60 | 1280 | 320 | 160 |
| 64 | 1280 | 160 | 320 |
| 67 | 640 | 160 | 160 |
| 67 | | 160 | 160 |
| 70 | | 160 | 160 |
| 72 | | 160 | 320 |
| 74 | | 160 | 160 |
| 77 | | 160 | 80 |
| 79 | | 160 | 80 |
| 81 | | 320 | 160 |
| 83 | | 320 | 80 |

The data of Table 4 show that cells bound to a porous microcarrier continuously produce HAV antigen over a long-term period of at least 83 days. Cells seeded on smooth microcarrier produces higher virus antigen titer at the beginning, but the cells showed tendency to aggregate after some time.

EXAMPLE 6

Long-term Propagation of Microcarrier Bound Serum Free or Serum and Protein Free VERO Cells For large scale production of HAV virus VERO cells grown under serum-free or serum- and protein-free culture medium conditions to a biomass of $1\times10^{11}$ are seeded on a porous microcarrier. Cells are infected with HAV with an m.o.i. of 0.1. Propagation of infected cells at 34° C. up to 350 days are performed with permanent perfusion of the cell culture medium. When virus antigen is detected in the medium, the virus containing supernatant is collected and stored at 4° C. The harvest of the serum free cell culture supernatant is started at days 35–45 after infection. The virus antigen obtained was calculated for an average production of vaccine doses from a 100 l fermenter per l of medium per 60 days and is summarized in Table 5.

TABLE 5

HAV production on VERO cells and calculation of productivity for 100 I Scale

| Lot run # | 1 | 2 | 3 | Mean value |
|---|---|---|---|---|
| Mean titer (EU/ml) | 640 | 978 | 461 | 693 |
| Volumetric production rate (EU/I/day) | 160.000 | 276.000 | 128.000 | 188.00 |
| No. of doses/I/day (gross) | 160 | 276 | 128 | 188 |
| No. of doses/I/day (net) | 32 | 55 | 26 | 38 |
| No. of doses in 100 days (net) | 320.000 | 552.000 | 260.00 | 380.000 |

EXAMPLE 7

Purification of HAV Antigen from Cell Culture Supernatant

The cell culture supernatant collected from the perfusion culture medium as described in Example 6 comprising HAV antigen is separated from the cellular debris by low speed centrifugation or depth filter, and concentrated by ultrafiltration using a 50 K Omega membrane (cut-off 50 000 Da, Filtron). The concentrate is further purified by centrifugation over a 20%–60% sucrose gradient and fractionated. Each fraction is tested for HAV antigen by a qualitative ELISA assay (Mediagnost). HAV antigen assembled in two peak fractions. The peak fractions are separately pooled and concentrated by high speed centrifugation.

During the process described above, the amount of antigen and the protein content is determined. The two peak pool fractions are analyzed by Western blot analysis with antibodies specific for HAV polypeptides VP0, VP1 and VP3 as well as a mixture thereof. The peak pool fractions 12–19 consist of mature virions (because of the presence of the capsid protein VP2 and the absence of VP0). The peak pool fractions 22–25 contain provirions and/or preprovirions.

This shows that by the process described HAV is continuously released in cell culture medium by persistently infected VERO cells grown in serum free or serum and protein free medium during large scale manufacturing process.

The respective fractions 12–19 and 22–25 are collected, the virus preparation is subjected to virus inactivation method and the inactivated preparation is formulated in a vaccine composition.

EXAMPLE 8

Purification of *Streptomyces griseus* Trypsin from Pronase a) Ion Exchange Chromatography 30 g of Pronase (Boehringer Ingelheim) was dissolved in Buffer A (0.02 pyridin, pH 5.0) to a final concentration of 40 mg/ml Pronase. 25 ml of the solution was subjected to cation exchange chromatography on CM Sepharose Cl 6B (Pharmacia) equilibrated with buffer A). The elution was performed at room temperature using a linear gradient with buffer A (0.02 M pryridin) and buffer B (0.75M pyridin pH 5.0) with 5 times the column volume.

Collected fractions were tested for inhibiting properties by mixing samples of the fractions with soy bean inhibitor in a 1:10 ratio (e.g. 1 mg soy bean inhibitor/100 $\mu$g protein) followed by a chromatographic substrate assay using S2222. The results were expressed as Δ absorbance units per minute (Δ A/min). The fraction having the highest inhibiting activity to soy bean inhibitor was further analysed by SDS-PAGE and stained with Coomassie.

The trypsin activity was measured by chromogenic assay using N-benzoyl-L-arginine ethyl ester (BAEE, in Tris buffer pH 8.0, 20 mM $CaCl_2$, 25° C.) as substrate and Δ absorbance units per minute is determined. As a control reference, porcine trypsin solution (1 mg/ml) with a specific activity of $13\times10^3$ U/mg was used. The specific activity was defined as the units of trypsin enzyme activity per mg protein. The results are summarized in Table 1.

The chymotrypsin activity was measured by chromogenic assay using 3-carboxymethoxypropionyl-L-arginyl-L-propyl-L-tyrosine-p-notroaniline hydrochloride (S-2586, Chromogenix). The results were expressed Δ absorbance units per minute (Δ A/min).

TABLE 6

Purification of Pronase by ion exchange chromatography

| Streptomyces griseus Pronase | Pronase unpurified | Purified fraction |
|---|---|---|
| Protein (g) | 1 | 0.08 |
| Specific activity U/mg | $1.6 \times 10^3$ | $16.5 \times 10^3$ |
| Recovery U in % | 100 | 70 |
| Stability by SDS-PAGE | n.d. | Unstable, low molecular weight fragmentation |
| Inhibition by soy bean inhibitor (% inhibition) | n.d. | 90 ± 0.1 |
| Chymotryspin activity (Δ A/min) | 450 | 38 |

*n.d. not determined

Table 6 shows that the fractions containing a protein having trypsin-like activity, as determined by inhibition test with soy bean inhibitor, can be purified by ion exchange chromatography with a specific activity which is about 10 times higher than of Pronase and with a recovery of about 70%. However, the protein is unstable and shows not a single band, but various bands in SDS-PAGE. This is indicative of fragmentation and autocleavage of the protein.

b) Affinity Chromatography on Immobilized Benzamidine

A Benzamidine Sepharose 6B fast flow (Pharmacia) column equilibrated with buffer A (50 mM Tris, 0.5 M NaCl pH 7.0) was loaded with 40 ml of a Pronase solution (75 mg/ml, buffer A). Elution was performed with Buffer B (50 mM Tris, 0.5 M NaCl pH 7.0, 10 mM benzamidine hydrochlorid pH 7.0), buffer C (0.5 M NaCl, 0.6 M arginine, pH 5.5) or buffer D (0.5 M NaCl, 1 M arginine, pH 5.5).

The fractions collected were tested for inhibiting properties using soy bean inhibitor, as well as trypsin and chymotrypsin activity as described in Example 8 A. The specific activity was determined as units of enzyme activity per mg protein.

TABLE 7

Purification of Pronase by affinity chromatography on immobilized benzamidine and elution with benzamidine

| Strepromyces griseus pronase | Pronase unpurified | Purified fraction |
|---|---|---|
| Affinity chromatography and elution with benzamidine (Buffer B) | | |
| Protein (g) | 3 | 0.13 |
| Specific activity U/mg | $1.6 \times 10^3$ | $19 \times 10^3$ |
| Recovery U in % | 100 | 60 |
| Stability by SDS-PAGE | stable | stable |
| Inhibition by soy bean inhibitor (% inhibition) | n.d. | 99.98 ± 0.1% |
| Chymotryspin activity (Δ A/min) | n.d. | 0.1 |

The results summarized in Table 7 show that by competitive elution with benzamidine, 60% of purified trypsin-like activity of Pronase was recovered with a specific activity of about 140 U/$\mu$g protein. However, the purified trypsin-like protease containing fraction is preferably further purified and the benzamidine removed prior to use in processes which involve cell culture growth or production of biologicals for application in humans.

TABLE 8

| Purification of Pronase by affinity chromatography on immobilized benzamidine and elution with 0.6 M arginine and 1 M arginine | | |
|---|---|---|
| Streptomyces griseus Pronase | Pronase unpurified | Purified fraction |
| Affinity chromatography and elution with 0.6 M arginine (Buffer C) | | |
| Protein (g) | 3 | 0.13 |
| Specific activity U/mg | $1.6 \times 10^3$ | $26 \times 10^3$ |
| Recovery U in % | n.d. | 63 |
| Stability by SDS-PAGE | stable | stable |
| Inhibition by soy bean inhibitor (% inhibition) | n.d. | 99.89 ± 0.1% |
| Chymotrypsin activity (Δ A/min) | n.d. | <0.1 |
| Affinity chromatography and elution with 1 M arginine (Buffer D) | | |
| Protein (g) | 3 | 0.13 |
| Specific activity U/mg | $1.6 \times 10^3$ | $46.5 \times 10^3$ |
| Recovery U in % | n.d. | 71% |
| Stability by SDS-PAGE | stable | stable |
| Inhibition by soy bean inhibitor (% inhibition) | n.d. | 99.99 ± 0.1% |
| Chymotrypsin activity (Δ A/min) | n.d. | <0.1 |
| LAL (EU/1000 U) | 88 | <4 |

As can be seen from results in Table 8, about 63% of the initial trypsin-like activity of Pronase was recovered when using a buffer comprising 0.6 M arginine, whereas about 71% is recovered with a buffer comprising 1M arginine. The purified SGT eluted with arginine from a benzamidine affinity carrier also had a higher specific activity compared to SGT obtained by ion exchange chromatography or elution with benzamidine from a benzamidine carrier. Further, a product of higher purity and specific activity was obtained when a buffer comprising increasing molarity of arginine was used.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method for continuous production of Hepatitis A virus (HAV) antigen, comprising the steps of providing a serum free cell culture of VERO cells bound to a microcarrier; growing the VERO cells in said serum free cell culture; infecting said serum free cell culture of VERO cells with HAV at a reduced temperature compared to the step of growing the cells; incubating said serum free cell culture of VERO cells infected with HAV to propagate said HAV at the reduced temperature, whereby HAV antigen is continuously released into the cell culture medium because infected cells release at least 50% of viral antigen into said medium; and harvesting said HAV antigen released into said medium.

2. The method according to claim 1, wherein said cells are grown at a temperature of about 37° C.

3. The method according to claim 1, wherein said temperature is reduced to about 34° C. prior to infection.

4. The method of claim 1, wherein the microcarrier is selected from the group of spherical or porous microcarriers.

5. The method according to claim 4, wherein the microcarriers comprise dextran, gelatine, collagen, plastic, or cellulose.

6. The method according to claim 1, wherein the cells are infected with HAV at a multiplicity of infection between about 0.01 and about 5.0.

7. The method according to claim 1, wherein the cell culture is subcultured from a working cell bank and passaged by use of a microbial protease or a trypsin-like enzyme of a microbial origin.

8. The method according to claim 7, wherein said microbial protease is the trypsin-like enzyme of Streptomyces griseus Pronase.

9. The method according to claim 1, wherein the cells bound to the microcarrier continuously produce and release HAV antigen into the cell culture medium for at least 60 days.

10. The method according to claim 1, wherein said serum free cell culture of VERO cells is a serum and protein free cell culture of VERO cells.

11. The method of claim 1, wherein the HAV antigen released into said medium is a complete HAV particle.

12. The method of claim 11, further comprising isolating the complete HAV particle from the HAV harvest.

13. The method of claim 12, wherein the complete HAV particle is isolated by isopycnic centrifugation.

* * * * *